US012616532B2

(12) United States Patent
Shindo

(10) Patent No.: US 12,616,532 B2
(45) Date of Patent: May 5, 2026

(54) MEDICAL ROBOT AND ATTACHMENT PORTION OF MEDICAL ROBOT

(71) Applicant: RIVERFIELD INC., Tokyo (JP)

(72) Inventor: Koki Shindo, Tokyo (JP)

(73) Assignee: RIVERFIELD INC., Tokyo (JP)

( * ) Notice: Subject to any disclaimer, the term of this patent is extended or adjusted under 35 U.S.C. 154(b) by 880 days.

(21) Appl. No.: 17/843,503

(22) Filed: Jun. 17, 2022

(65) Prior Publication Data

US 2022/0313376 A1      Oct. 6, 2022

Related U.S. Application Data

(63) Continuation of application No. PCT/JP2020/035758, filed on Sep. 23, 2020.

(30) Foreign Application Priority Data

Dec. 20, 2019      (JP) ................................. 2019-230907

(51) Int. Cl.
*A61B 34/30*          (2016.01)
*B25J 9/00*           (2006.01)

(52) U.S. Cl.
CPC .............. *A61B 34/30* (2016.02); *B25J 9/0009* (2013.01)

(58) Field of Classification Search
CPC .......... A61B 34/30; A61B 2017/00477; A61B 2034/302; B25J 9/0009
See application file for complete search history.

(56) References Cited

U.S. PATENT DOCUMENTS

2006/0161138 A1      7/2006  Orban, III et al.
2015/0265355 A1      9/2015  Prestel et al.

2017/0027656 A1      2/2017  Robert et al.
2019/0159853 A1      5/2019  Haraguchi et al.
2019/0269471 A1*     9/2019  Phoolchund ......... A61B 17/072

FOREIGN PATENT DOCUMENTS

CN      102630154 A      8/2012
CN      107028660 A      8/2017
JP        5807974 B2    11/2015
JP      2018-504285 A    2/2018
JP      2018-191881 A   12/2018
JP      2019-529020 A   10/2019

OTHER PUBLICATIONS

International Search Report for PCT/JP2020/035758 dated Nov. 24, 2020 [PCT/ISA/210].

* cited by examiner

*Primary Examiner* — Brooke Labranche
*Assistant Examiner* — Rachael L Geiger
(74) *Attorney, Agent, or Firm* — Sughrue Mion, PLLC

(57) ABSTRACT

A medical robot includes a surgical tool and an attachment portion. The surgical tool has a main body that includes a driven portion that transmits a driving force, and a driven side hole. The attachment portion has an attachment surface and a transmission side hole is arranged in which a transmission plate transmits the driving force in a linear motion direction to the driven portion. The surgical tool and the attachment portion respectively include a surgical tool engagement portion and an attachment engagement portion that engage to attach the surgical tool to the attachment portion by relative movement in a relative movement direction along the attachment surface and intersecting the linear motion direction. The attachment surface includes a guide groove that guides the driven portion to a specified position of the transmission side hole.

17 Claims, 6 Drawing Sheets

MEDICAL ROBOT AND ATTACHMENT PORTION OF MEDICAL ROBOT

CROSS-REFERENCE TO RELATED APPLICATIONS

This Application is a continuation of International Application No. PCT/JP2020/035758 filed Sep. 23, 2020 which is based on and claims priority from Japanese Patent Application No. 2019-230907 filed on Dec. 20, 2019 with the Japan Patent Office, the contents of each of which being herein incorporated by reference in their entireties.

BACKGROUND

1. Field

The present disclosure relates to a medical robot to be used for treatment of patients and an attachment portion of the medical robot.

2. Description of the Related Art

In recent years, medical treatment using a robot has been proposed in order to achieve reduction in workload on operators and labor saving in medical facilities. In the field of surgery, there has been a proposal of a medical robot with which an operator performs treatment of a patient by a multi-degree-of-freedom manipulator including a remotely controllable multi-degree-of-freedom arm.

SUMMARY

It is an aspect to provide a medical robot and an adapter thereof having improved operability and a simplified configuration.

According to an aspect of one or more embodiments, there is provided a medical robot comprising a surgical tool comprising a main body comprising a driven portion configured to transmit a driving force to a treatment portion for performing a medical treatment; and a driven side hole in which the driven portion is housed and in which the driven portion is arranged so as to be linearly movable; and an attachment portion comprising an attachment surface configured to face a surface of the main body in which the driven side hole is provided; and a transmission side hole in which a transmission plate is arranged that transmits the driving force in a linear motion direction to the driven portion, wherein the surgical tool and the attachment portion respectively comprise a surgical tool engagement portion and an attachment engagement portion configured to attach the surgical tool to the attachment portion by relative movement of the surgical tool and the attachment portion in a relative movement direction along the attachment surface and intersecting the linear motion direction, and wherein the attachment surface comprises a guide groove extending in the relative movement direction and configured to engage with a projection projecting from the driven portion when attaching the surgical tool to the attachment portion, thereby guiding the driven portion to a specific position of the transmission side hole.

According to another aspect of one or more embodiments, there is provided a An adapter of a medical robot, the adapter being configured to be attached to a surgical tool, the adapter comprising an attachment surface configured to face a surface of a main body of the surgical tool in which a driven side hole is provided; a transmission side hole in which a transmission plate is arranged to transmit a driving force in a linear motion direction to a driven portion of the surgical tool; an attachment engagement portion configured to receive the surgical tool by relative movement of the surgical tool and the adapter in an intersection direction along the attachment surface that intersects the linear motion direction; and a guide groove provided in the attachment surface and extending in the intersection direction, and configured to, when the surgical tool is attached to the adapter, engage with a projection of the driven portion to guide the driven portion to a position of the transmission side hole.

According to yet another aspect of one or more embodiments, there is provided a medical robot comprising a surgical tool and an adapter. The surgical tool comprises a main body comprising a driven plate that transmits a driving force to a treatment portion; a first hole in which the driven plate is housed and in which the driven plate is movable in a linear direction; a projection provided on the driven plate; and an engagement projection provided at a distal end of the main body, the engagement projection extending in an intersecting direction that intersects with the linear direction. The adapter comprises a transmission plate configured to transmit the driving force to the driven plate; a second hole in which the transmission plate is housed and in which the transmission plate is movable in the linear direction; a guide groove that extends in the intersecting direction; and an engagement groove provided at a distal end of the adapter, the engagement groove extending in the intersecting direction. The surgical tool is configured to be attached to the adapter by relative movement in the intersecting direction and, when the surgical tool is attached to the adapter, the guide groove engages with the projection and the engagement groove engages with the engagement projection to guide the driven plate to a position within the second hole.

BRIEF DESCRIPTION OF THE DRAWINGS

The above and other aspects will be more clearly understood from the following detailed description, taken in conjunction with the accompanying drawings, in which.

DETAILED DESCRIPTION

Figure 1:
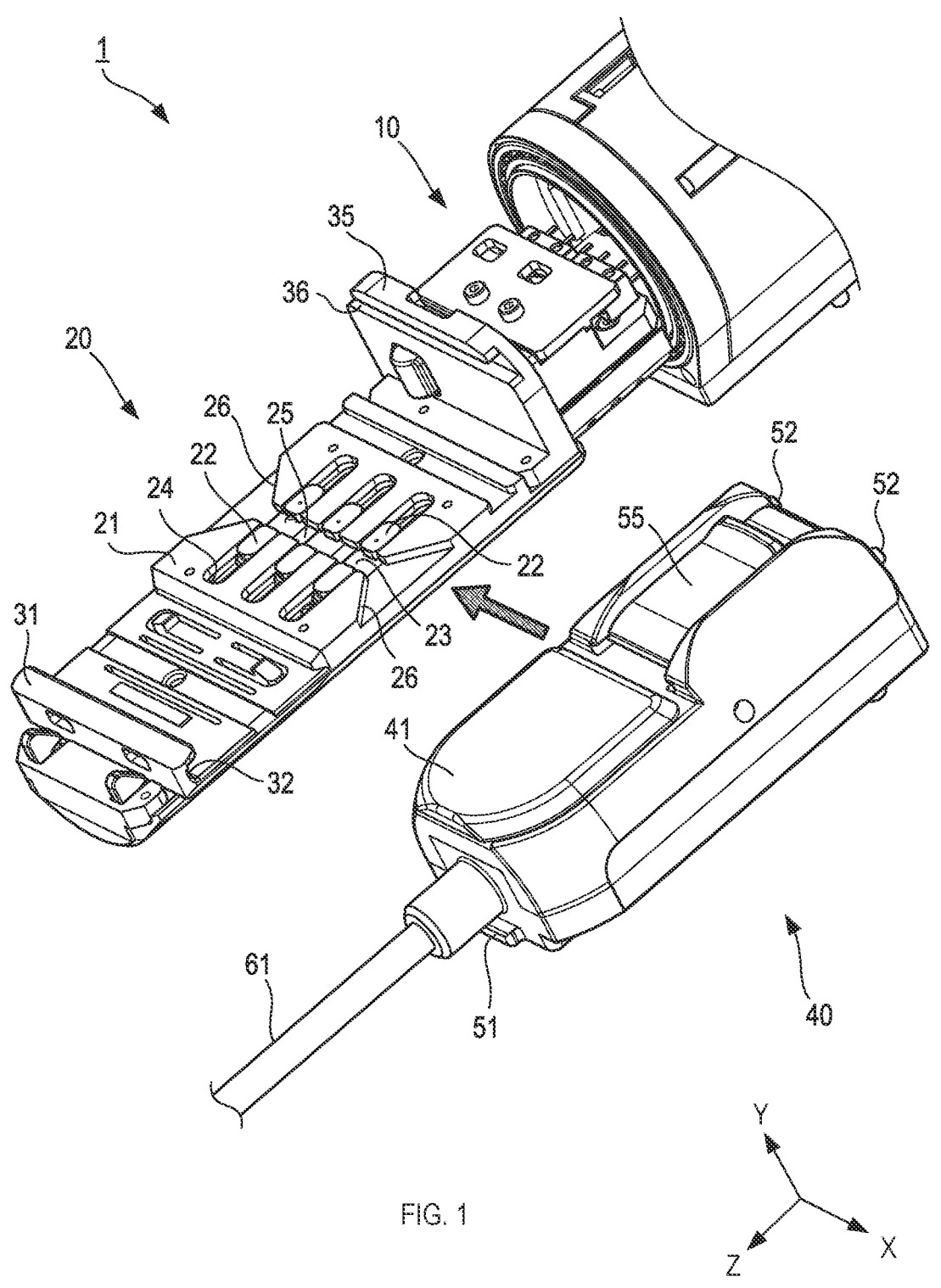
FIG. 1 is a partial perspective view illustrating a configuration of a medical robot according to an embodiment.

According to a related art technique, a surgical tool to be used for treatment is attachable to and detachable from a medical robot. Also, a driving force to drive a movable part of the surgical tool is transmitted from the medical robot to the surgical tool.

Further, there is provided a transmission configuration configured to transmit a driving force from the medical robot to the surgical tool to be used for treatment when attaching the surgical tool to the medical robot. The transmission configuration is configured so as to be engaged and released in response to attachment and detachment of the surgical tool to and from the medical robot.

Specifically, a configuration is disclosed in which engagement is established so as to allow transmission of a driving force using a biasing force of a spring when the surgical tool is attached to and detached from the medical robot. This configuration allows replacement of the surgical tool while performing treatment.

According to the related art technique, however, the transmission configuration is required to allow movement due to biasing force since biasing force of the spring is used for engagement. In other words, it is required to intentionally provide a play, looseness, or gap in the transmission configuration.

Thus, it is difficult to reduce occurrence of a gap, which does not contribute to transmission of a driving force, in a path to transmit the driving force in the transmission configuration. A problem has been found that this gap makes it difficult to accurately control actions of the surgical tool.

Also, in order for an operator to operate the medical robot to move the surgical tool just as intended, it is necessary to detect whether engagement is established in the transmission configuration so as to allow transmission of a driving force. Specifically, it is necessary to detect engagement using a detection device, such as a sensor or a switch, and to provide wiring or the like to transmit detected information to the operator. That is, a problem has been found that the medical robot has a complicated configuration.

In one aspect of the present disclosure, a medical robot is provided that facilitates improved operability and simplified configuration and to provide an adapter of a medical robot.

A medical robot in a first aspect of the present disclosure comprises: a surgical tool at least comprising: a main body that comprises a driven portion configured to transmit a driving force to a treatment portion for performing a medical treatment; and a driven side hole in which the driven portion is housed and the driven portion is arranged so as to be relatively linearly movable; and an attachment portion at least comprising: an attachment surface configured to face a surface of the main body in which the driven side hole is provided; and a transmission side hole in which a transmission plate to transmit a driving force in a linear motion direction to the driven portion is arranged. The surgical tool and the attachment portion respectively comprise a surgical tool engagement portion and an attachment engagement portion configured to attach the surgical tool to the attachment portion by relative movement of the surgical tool and the attachment portion in a direction along the attachment surface and intersecting the linear motion direction, and the attachment surface comprises a guide groove extending in a direction in which the surgical tool relatively moves with respect to the attachment portion and configured to engage with a projection projecting from the driven portion when attaching the surgical tool to the attachment portion, thereby guiding the driven portion to a specified position of the transmission side hole.

An attachment portion in a second aspect of the present disclosure is an attachment portion, to which a surgical tool is attached, the surgical tool at least comprising a main body that comprises a driven portion configured to transmit a driving force to a treatment portion for performing a medical treatment; and a driven side hole in which the driven portion is housed and the driven portion is arranged so as to be relatively linearly movable. The attachment portion at least comprises: an attachment surface configured to face a surface of the main body in which the driven side hole is provided; a transmission side hole in which a transmission plate to transmit a driving force in a linear motion direction to the driven portion is arranged; an attachment engagement portion configured to attach the surgical tool to the attachment portion by relative movement of the surgical tool and the attachment portion in a direction along the attachment surface and intersecting the linear motion direction; and a guide groove provided in the attachment surface and extending in a direction in which the surgical tool relatively moves with respect to the attachment portion, and configured to engage with a projection projecting from the driven portion when attaching the surgical tool to the attachment portion, thereby guiding the driven portion to a specified position of the transmission side hole.

According to the medical robot in the first aspect and the attachment portion in the second aspect of the present disclosure, the surgical tool may be attached to the attachment portion by relative movement of the surgical tool and the attachment portion in a direction along the attachment surface and intersecting the linear motion direction of the driven portion and the transmission plate. Also, when attaching the surgical tool to the attachment portion, the driven portion is guided to a specified position of the transmission side hole. The specified position is a position at which the driven portion and the transmission plate engage with each other in response to attachment of the surgical tool to the attachment portion. Accordingly, the transmission plate and the driven portion engage with each other so as to allow transmission of the driving force.

For example, as compared with a related art configuration, the transmission plate and the driven portion may be engaged with each other with a simple configuration since there is no need to use a biasing mechanism. Further, there is less need to provide a gap between the transmission plate and the driven portion, and thus secure engagement therebetween is facilitated.

Accordingly, the gap may be reduced, thereby facilitating increase in operability of the medical robot. Moreover, reduction of the gap facilitates transmission of an external force, which is a force applied to the treatment portion of the surgical tool, to the medical robot, and facilitates increase in accuracy when estimating an external force. For example, it is possible to facilitate increase in safety of surgeries using the medical robot, and to facilitate reducing occurrence of complications. In other words, it is possible to facilitate improved QOL of patients, and to facilitate reducing burden on doctors who operate the medical robot. Moreover, it is possible to facilitate achievement of an improved learning curve in surgeries using the medical robot. "QOL", as referred to herein, is an abbreviation of "Quality of Life".

In addition, it is possible to determine whether an arrangement relationship between the transmission plate and the driven portion is a desired arrangement relationship based on the relative position of the surgical tool and the attachment portion. Examples of the desired arrangement relationship may include an arrangement relationship that allows transmission of a driving force. In other words, there is less need to use a detection device, such as a sensor or a switch, than in the configuration disclosed in Patent Document 1. Accordingly, it is possible to reduce complication of the configuration caused by providing a detection device, and to facilitate downsizing of the medical robot.

In the first aspect, it is advantageous that an introducing groove is provided at least at one end of the guide groove along a relative movement direction of the surgical tool and the attachment portion, the introducing groove having a greater groove width in a direction away from the transmission side hole.

By providing the introducing groove to the guide groove, the projection of the driven portion is guided by the introducing groove and thus easily enters the guide groove when attaching the surgical tool to the attachment portion. Also, in a case where the introducing groove is provided at each of both ends of the guide groove, there is an increased degree of freedom in terms of an approaching direction of the surgical tool to the attachment portion, as compared with a case of being provided at one end, and thus attachment of the surgical tool is facilitated.

In the first aspect, it is advantageous that a mover configured to move the transmission plate to the specified position is provided.

By providing the mover, the transmission plate may be easily arranged at the specified position when attaching the surgical tool to the attachment portion. As compared with a case without the mover, workload may be reduced when attaching the surgical tool to the attachment portion, and thus the attachment is facilitated.

In the first aspect, it is advantageous that a plurality of the transmission side holes and a plurality of the transmission plates are provided in the attachment portion side by side along the relative movement direction of the surgical tool and the attachment portion, and that a plurality of the driven side holes and a plurality of the driven portions are provided in the main body so as to correspond to at least a part of the plurality of the transmission side holes and the plurality of the transmission plates.

With this configuration, it is possible to transmit different driving forces to the treatment portion using a plurality of combinations of the transmission plates and the driven portions. Accordingly, it is possible to control a plurality of actions of the treatment portion.

In the first aspect, it is advantageous that the transmission plate comprises a recessed portion configured to engage with the projection of the driven portion in response to attachment of the surgical tool to the attachment portion, the recessed portion including an opening that allows the projection to move along the relative movement direction of the surgical tool and the attachment portion.

By providing the recessed portion, it is possible to engage the projection of the driven portion with the recessed portion of the transmission plate when the surgical tool is attached to the attachment portion. Also, it is possible to transmit a driving force from the transmission plate to the driven portion based on engagement of the projection with the recessed portion.

According to the medical robot in the first aspect of the present disclosure and the attachment portion in the second aspect of the present disclosure, an effect is achieved that improved operability and simplified configuration may be facilitated by providing the guide groove configured to engage with the projection projecting from the driven portion, thereby guiding the driven portion to a specified position of the transmission side hole.

Various example embodiments will be described more fully hereinafter with reference to the accompanying drawings, in which embodiments are shown.

A description will be given of a medical robot according to various embodiments with reference to FIG. 1 to FIG. 6. A medical robot 1 of the various embodiments is a multi-degree-of-freedom manipulator having a multi-degree-offreedom arm that is remotely controllable, and is used when an operator performs treatment of a patient, such as endoscopic surgery.

As shown in FIG. 1, the medical robot 1 comprises a driver 10, an adapter 20, and a surgical tool 40. The adapter 20 corresponds to one example configuration of an attachment portion.

To simplify the description of the present embodiment, a direction in which the driver 10 extends is defined as a Z-axis, and a direction toward a leading end of the driver 10 is defined as a positive direction of the Z-axis. Also, in the description, a direction which is orthogonal to the Z-axis and along which the surgical tool 40 is relatively moved when being attached to the adapter 20 is defined as an X-axis, and a left direction with respect to a positive direction of the Z-axis is defined as a positive direction of the X-axis. Further, in the description, a direction orthogonal to the Z-axis and the X-axis is defined as a Y-axis and a direction along which the surgical tool 40 is relatively moved when being detached from the adapter 20 is defined as a positive direction of the Y-axis.

The driver 10 supports the adapter 20 and the surgical tool 40 and transmits a driving force to actuate the surgical tool 40. In the present embodiment, a portion of the driver 10 where the adapter 20 is arranged is rotatably arranged around an axis extending in the Z-axis direction.

Figure 2:
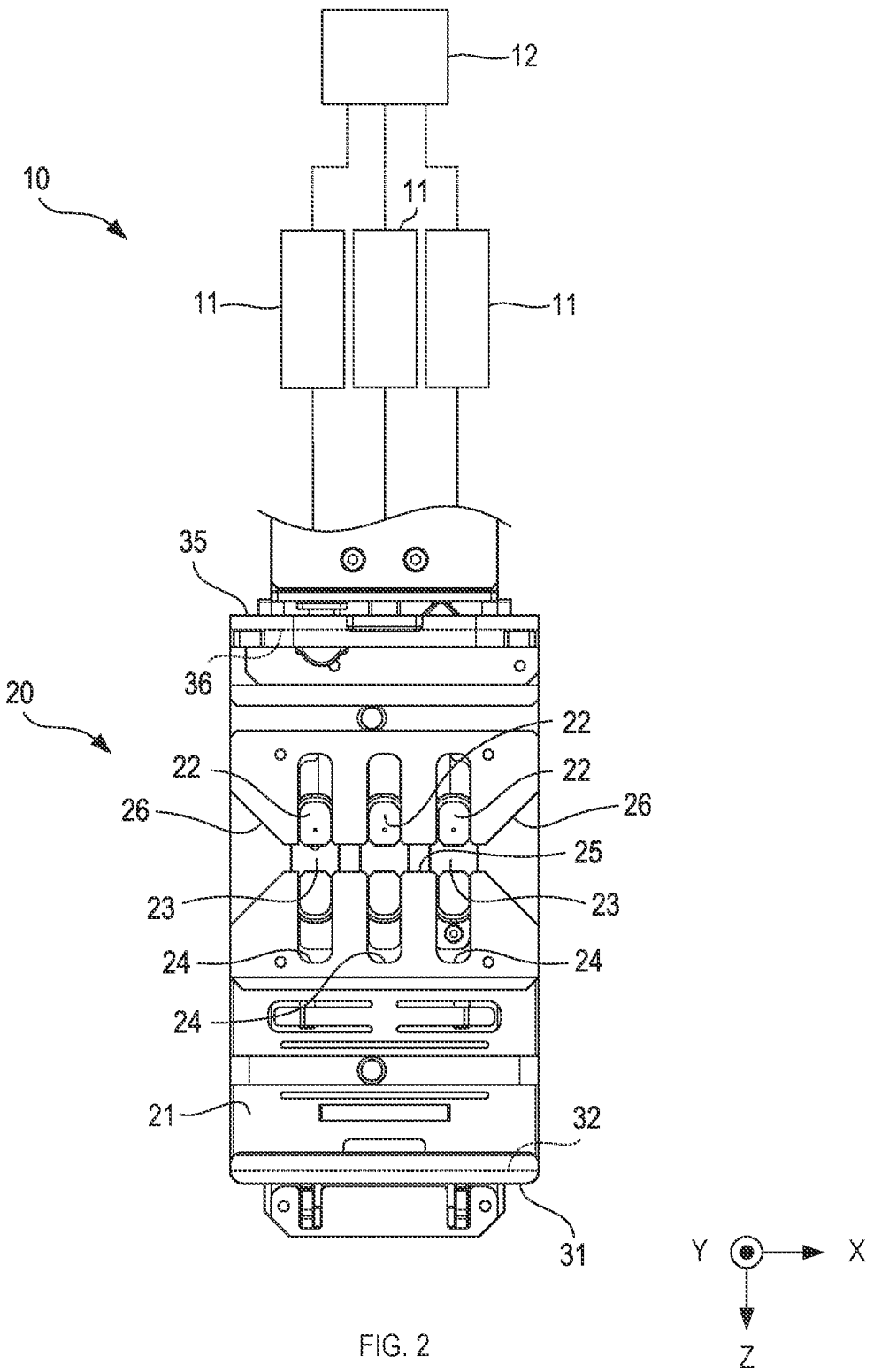
FIG. 2 is a view illustrating a configuration of an arm portion and an adapter of the medical robot of FIG. 1, according to an embodiment.

As shown in FIG. 1 and FIG. 2, the driver 10 comprises actuators 11 and a controller 12. The actuator 11 corresponds to one example configuration of a mover.

At least one of the actuator 11 or the controller 12 may be provided in the driver 10 or may be provided outside the driver 10, and its arrangement position is not limitative.

The actuator 11 generates a driving force to actuate the surgical tool 40. The actuator 11, which is connected to a later described transmission plate 22 of the adapter 20 such that the driving force may be transmitted to the transmission plate 22, moves the transmission plate 22 in the positive direction and a negative direction of the Z-axis.

In the present embodiment, the actuator 11 generates the driving force using a gas, such as air, or a fluid. The actuator 11 may employ an electric motor, and there is no limitation to a form of generating its power.

Further, the actuator 11 may be configured with a piston and a cylinder, or may be configured to generate the driving force using another fluid, and there is no limitation to a specific configuration.

The controller 12 controls generation of the driving force in the actuator 11. The controller 12 also controls movement of the transmission plate 22 in the positive direction and the negative direction of the Z-axis, and controls an arrangement position of the transmission plate 22. In the present embodiment, the controller 12 controls supply of a gas, such as air, to the actuator 11.

As shown in FIG. 1 and FIG. 2, the adapter 20 is arranged between the driver 10 and the surgical tool 40. The adapter 20 is attachable to and detachable from the driver 10, and is also attachable to and detachable from the surgical tool 40.

The adapter 20 also serves to separate an unclean region on a side of the driver 10 and a clean region on a side of the surgical tool 40. The adapter 20 comprises a not-shown drape that is a film-shaped member to separate the unclean region from the clean region.

The adapter 20 comprises at least an attachment surface 21, a first attachment engagement portion 31, and a second attachment engagement portion 35. The first attachment engagement portion 31 and the second attachment engagement portion 35 each correspond to one example configuration of an attachment engagement portion.

The attachment surface 21 is a surface of the adapter 20 on which the surgical tool 40 is arranged and which faces a surface, in which driven side holes 42 are formed, of a main body 41 of the surgical tool 40 described later. The first attachment engagement portion 31 is provided at an end of the attachment surface 21 in the positive direction of the Z-axis, and the second attachment engagement portion 35 is provided at an end of the attachment surface 21 in the negative direction of the Z-axis.

The adapter 20 further comprises at least the transmission plates 22, transmission side holes 24, a guide groove 25, and an introducing groove 26.

The transmission plate 22 transmits a driving force to the surgical tool 40. In the present embodiment, the transmission plate 22 moves within the transmission side hole 24 in the positive direction and the negative direction of the Z-axis, to thereby transmit the driving force.

The transmission plate 22 comprises a recessed portion 23 configured to engage with a later-described projection 44 of the surgical tool 40. The recessed portion 23 is a recess formed in a surface of the transmission plate 22 to face the surgical tool 40, in other words, a surface located in the positive direction of the Y-axis.

The recessed portion 23 has a groove shape extending along the positive direction and the negative direction of the Y-axis. In other words, the recessed portion 23 includes an opening that allows the projection 44 to enter the recessed portion 23 from the positive direction and come out from the negative direction of the Y-axis.

Side walls of the recessed portion 23 on a positive direction side and a negative direction side of the Z-axis are shaped to abut the projection 44. In other words, the side walls are shaped so as to transmit movement of the transmission plate 22 in the positive direction and the negative direction of the Z-axis to the projection 44.

The transmission side hole 24 is a through-hole in which the transmission plate 22 is arranged relatively movably, and is configured to allow movement of the transmission plate 22 in a direction along the attachment surface 21, in other words, configured to avoid deviation of the transmission plate 22 from the transmission side hole 24. The transmission side hole 24 is shaped as an elongated hole extending in a direction along the Z-axis. In the present embodiment, three transmission side holes 24 are arranged apart from one another in an X-axis direction.

Although there are three sets of the transmission plates 22 and the transmission side holes 24 in the present embodiment, the number of sets of the transmission plates 22 and the transmission side holes 24 may be greater than three, or may be less than three, and the number is not limited.

The guide groove 25, which is a recess formed in the attachment surface 21, is a groove to be used for guiding the projection 44 of a driven portion 43 described later. The guide groove 25 extends in a direction of relative movement of the surgical tool 40 with respect to the attachment surface 21. In the present embodiment, the guide groove 25 extends in a direction intersecting the transmission side hole 24, for example, in a direction along the X-axis.

The introducing groove 26 is a groove formed at each of a first end and a second end of the guide groove 25 so as to be continuous to the guide groove 25, and has a shape with a greater groove width in a direction away from the transmission side hole 24. It is desirable that a width of an opening portion of the introducing groove 26, in other words, a width at both ends thereof in the positive direction and the negative direction of the X-axis is large so as to include at least a moving range of the projection 44 in the transmission plate 22. Although the introducing groove 26 is provided at each of both ends of the guide groove 25 in the present embodiment, the introducing groove 26 may be provided only at the first end or the second end of the guide groove 25.

The first attachment engagement portion 31 is formed at an end of the attachment surface 21 of the adapter 20 in the positive direction of the Z-axis so as to protrude in the positive direction of the Y-axis. The first attachment engagement portion 31 abuts the surgical tool 40 arranged on the attachment surface 21, to thereby restrict movement of the surgical tool 40 in the positive direction of the Z-axis.

The first attachment engagement portion 31 comprises a surface to face the surgical tool 40 and the surface comprises a first engagement groove 32. The first engagement groove 32 is a groove opening in the negative direction of the Z-axis and extending along the X-axis. The first engagement groove 32 engages with a later-described first surgical tool engagement portion 51 of the surgical tool 40, to thereby restrict movement of the surgical tool 40 in directions along the Y-axis.

The second attachment engagement portion 35 is formed so as to protrude in the positive direction of the Y-axis from the end of the attachment surface 21 of the adapter 20 in the negative direction of the Z-axis. The second attachment engagement portion 35 abuts the surgical tool 40 arranged on the attachment surface 21, to thereby restrict movement of the surgical tool 40 in the negative direction of the Z-axis.

The second attachment engagement portion 35 comprises a surface to face the surgical tool 40 and the surface comprises a second engagement groove 36. The second engagement groove 36 is a groove opening in the positive direction of the Z-axis and extending along the X-axis. The second engagement groove 36 engages with a later-described second surgical tool engagement portion 52 of the surgical tool 40, to thereby restrict movement of the surgical tool 40 in the directions along the Y-axis.

Figure 3:
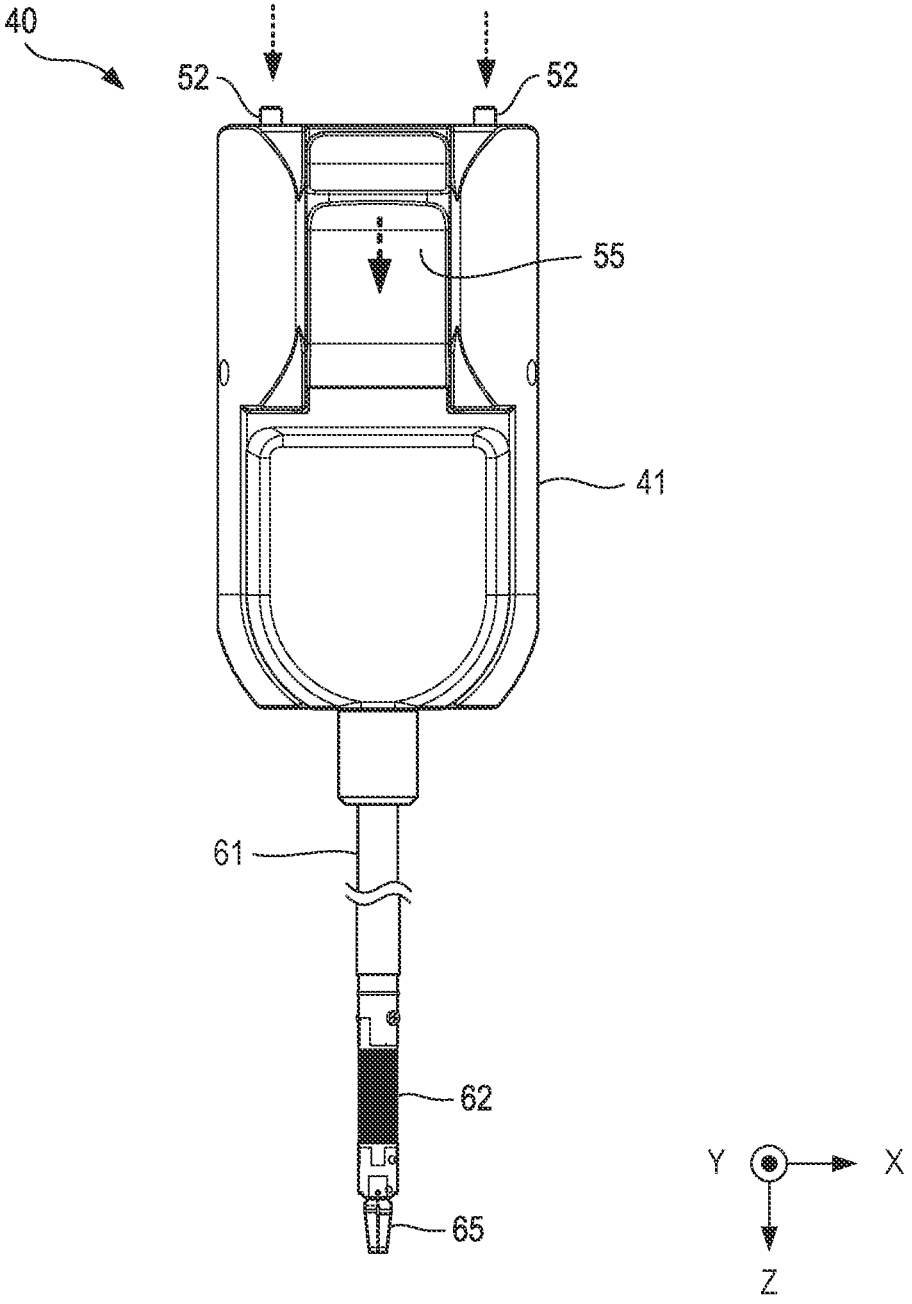
FIG. 3 is a view illustrating a configuration of a surgical tool of the medical robot of FIG. 1, according to an embodiment.
Figure 4:
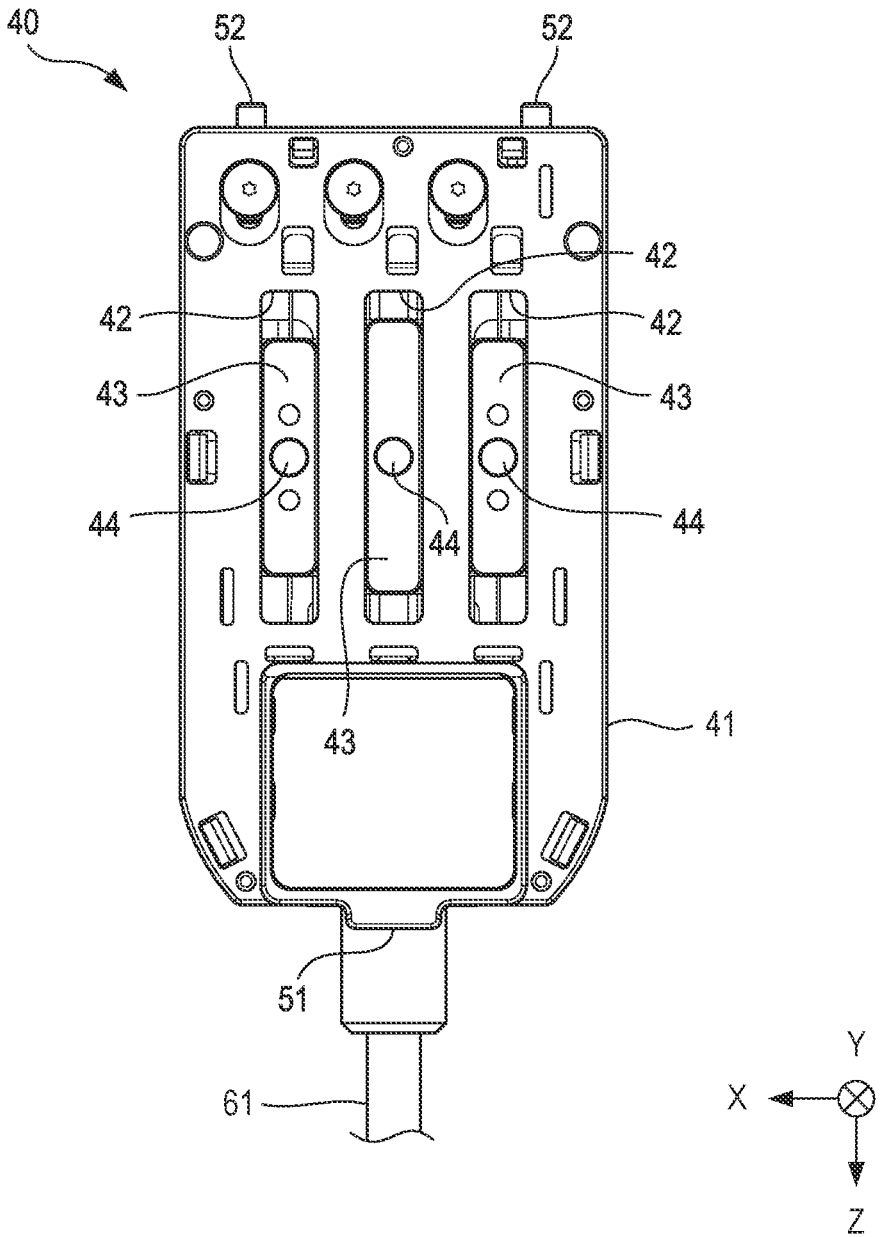
FIG. 4 is another view illustrating the configuration of the surgical tool of the medical robot of FIG. 1, according to an embodiment.

The surgical tool 40 is used when an operator performs treatment of a patient using the medical robot 1. As shown in FIG. 3 and FIG. 4, the surgical tool 40 comprises a main body 41, a shaft 61 extending in a rod shape from the main body 41, and a forceps 65 arranged at an end of the shaft 61 opposite to the main body 41. The forceps 65 corresponds to one example configuration of a treatment portion.

The main body 41 is a portion of the surgical tool 40 configured to be attached to and detached from the driver 10 and also configured to support the shaft 61. The main body 41 comprises the driven side holes 42, the driven portions 43, the first surgical tool engagement portion 51, the second surgical tool engagement portions 52, and an operation portion 55. The first surgical tool engagement portion 51 and the second surgical tool engagement portion 52 each correspond to one example configuration of a surgical tool engagement portion.

The driven side hole 42 is an elongated hole formed in a surface of the main body 41 to face the attachment surface 21 of the driver 10 and extending in the Z-axis direction. The driven side hole 42 is provided in a position to face the transmission side hole 24. The driven portion 43 to be described later is arranged in the driven side hole 42 so as to be relatively linearly movable with respect to the main body 41 in the Z-axis direction. In the present embodiment, the three driven side holes 42 are arranged apart from one another in the X-axis direction.

A driving force to move, for example, the forceps 65 is transmitted from the driver 10 to the driven portion 43. The driven portion 43 is arranged to be linearly movable in the Z-axis direction within the driven side hole 42 according to the driving force transmitted from a surgical robot.

The driven portion 43 comprises a projection 44. The projection 44 has a columnar shape projecting from the driven portion 43 in the negative direction of the Y-axis, and projects further than the main body 41 in the negative direction of the Y-axis when the driven portion 43 is arranged in the driven side hole 42. The projection 44 engages with the recessed portion 23 provided to the transmission plate 22 in the adapter 20, to thereby transmit a driving force for linear movement in the Z-axis direction.

As shown in FIG. 4, the first surgical tool engagement portion 51 is a protrusion provided at an end of the main body 41 in the positive direction of the Z-axis. The first surgical tool engagement portion 51 engages with the first engagement groove 32 of the first attachment engagement portion 31, to thereby restrict movement of the surgical tool 40 in the directions along the Y-axis.

As shown in FIG. 3 and FIG. 4, the second surgical tool engagement portions 52 are two protrusions provided at an end of the main body 41 in the negative direction of the Z-axis. The second surgical tool engagement portions 52 engage with the second engagement groove 36 of the second attachment engagement portion 35, to thereby restrict movement of the surgical tool 40 in the directions along the Y-axis.

The operation portion 55 is a portion to be used when causing the second surgical tool engagement portions 52 to be housed in the main body 41 and to protrude from the main body 41. The operation portion 55 is provided on a surface of the main body 41 on a positive direction side of the Y-axis and in an area on a negative direction side of the Z-axis.

The operation portion 55 is arranged to be relatively movable along the Z-axis with respect to the main body 41. For example, when the operation portion 55 is relatively moved in the positive direction of the Z-axis with respect to the main body 41, the second surgical tool engagement portions 52 are housed in the main body 41. Conversely, when the operation portion 55 is moved in the negative direction of the Z-axis with respect to the main body 41, the second surgical tool engagement portions 52 protrude from the main body 41.

As shown in FIG. 3 and FIG. 4, the shaft 61 is a tubular shaped member arranged to extend from the main body 41 in the Z-axis direction. The forceps 65 is arranged at the end of the shaft 61 in the positive direction of the Z-axis. Also, a joint 62 is provided to the shaft 61 in a vicinity of the forceps 65.

The joint 62 is configured to allow changes in orientation of the forceps 65 and configured to be rotatable about the X-axis direction as a rotation axis and about the Y-axis direction as a rotation axis. The joint 62 is configured, for example, so as to be rotated by the driving force transmitted by the power transmission plate 22. It is to be noted that there is no particular limitation to the configuration of the joint 62.

The forceps 65 is arranged at the end of the shaft 61 in the positive direction of the Z-axis, and is configured to be opened and closed by a driving force transmitted from the driven portion 43 through a wire or the like. There is no particular limitation to the configuration to open and close the forceps 65.

Next, a description will be given of attachment and detachment of the surgical tool 40 in the medical robot 1 configured as above with reference to FIG. 1, FIG. 2, FIG. 5, and FIG. 6. A case of attaching the surgical tool 40 to the adapter 20 will be first described, and then a case of detaching the surgical tool 40 from the adapter 20 will be described.

When attaching the surgical tool 40 to the adapter 20, the controller 12 performs control to drive the actuators 11 such that the transmission plates 22 are arranged at specified positions, as shown in FIG. 2. Once the transmission plates 22 are arranged at specified positions, the recessed portions 23 of the transmission plates 22 and the guide groove 25 form a groove extending in the direction along the X-axis.

The specified positions here mean positions where the recessed portions 23 of the transmission plates 22 are arranged at positions at which the guide groove 25 and the transmission side holes 24 intersect. In other words, the driven portions 43 engage with the transmission plates 22 at the specified position in response to attachment of the surgical tool 40 and the adapter 20. Specifically, arrangement positions of the transmission plates 22 shown in FIG. 2 are specified positions.

Thereafter, as shown in FIG. 1, the surgical tool 40 is moved in the direction along the X-axis to be closer to the adapter 20, and attachment is performed. FIG. 1 shows an example of attachment by moving the surgical tool 40 from the positive side to the negative side of the X-axis. Attachment may be performed by moving the surgical tool 40 closer to the adapter 20 from the negative side to the positive side of the X-axis.

During attachment, the first surgical tool engagement portion 51 of the surgical tool 40 moves in the direction along the X-axis into engagement with the first engagement groove 32 of the adapter 20. Also, the second surgical tool engagement portions 52 move in the direction along the X-axis into engagement with the second engagement groove 36 of the adapter 20.

Figure 5:
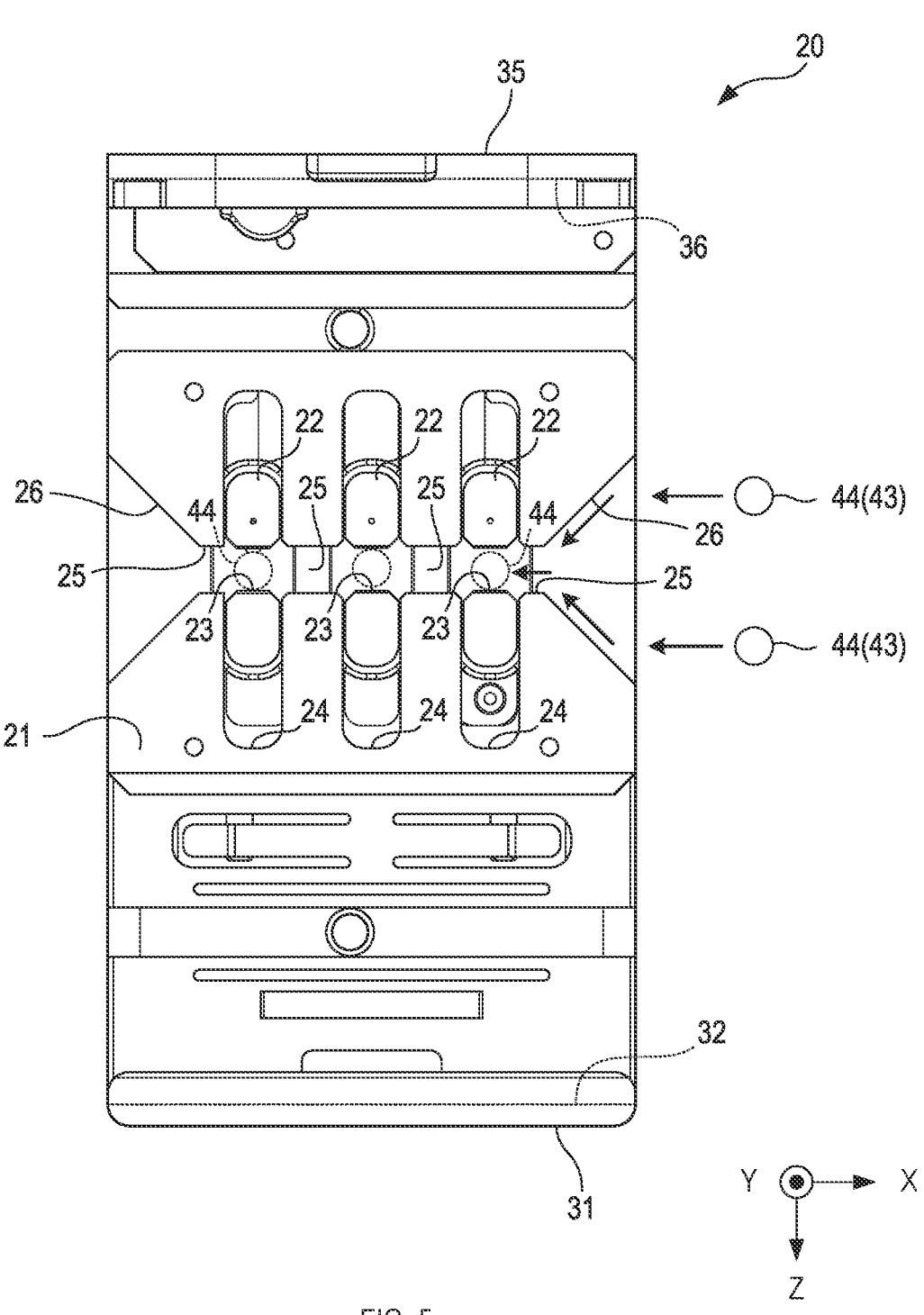
FIG. 5 is a view illustrating actions of driven portions and projections when attaching the surgical tool to the adapter, according to an embodiment.

Further, as shown in FIG. 5, the driven portions 43 of the surgical tool 40 are guided by the guide groove 25 and the introducing groove 26 to positions allowing transmission of a driving force with the transmission plate 22. A description will be given of an example case where the driven portions 43 are arranged apart from the guide groove 25 on the positive direction side or the negative direction side of the Z-axis.

When the surgical tool 40 approaches the adapter 20 along the X-axis, the projections 44 of the driven portions 43 each abuts an oblique surface of the introducing groove 26. When the surgical tool 40 is further moved, the projections 44 move toward the guide groove 25 along the oblique surface of the introducing groove 26, and enter the groove formed by the guide groove 25 and the recessed portions 23.

When the surgical tool 40 moves to a previously specified position relative to the adapter 20, the projections 44 are arranged in the recessed portions 23. In other words, the projections 44 are arranged in positions indicated by dotted lines in FIG. 5. As a result, the transmission plates 22 and the driven portions 43 are engaged to allow transmission of driving forces, and attachment between the surgical tool 40 and the adapter 20 is completed.

In the case of detaching the surgical tool 40 from the adapter 20, an operation is first performed of sliding the operation portion 55 of the surgical tool 40 in the positive direction of the Z-axis, as shown in FIG. 3. By this operation, the second surgical tool engagement portions 52 are housed in the main body 41. As a result of this operation, engagement between the second surgical tool engagement portions 52 and the second engagement groove 36 is released, as shown in FIG. 6.

Figure 6:
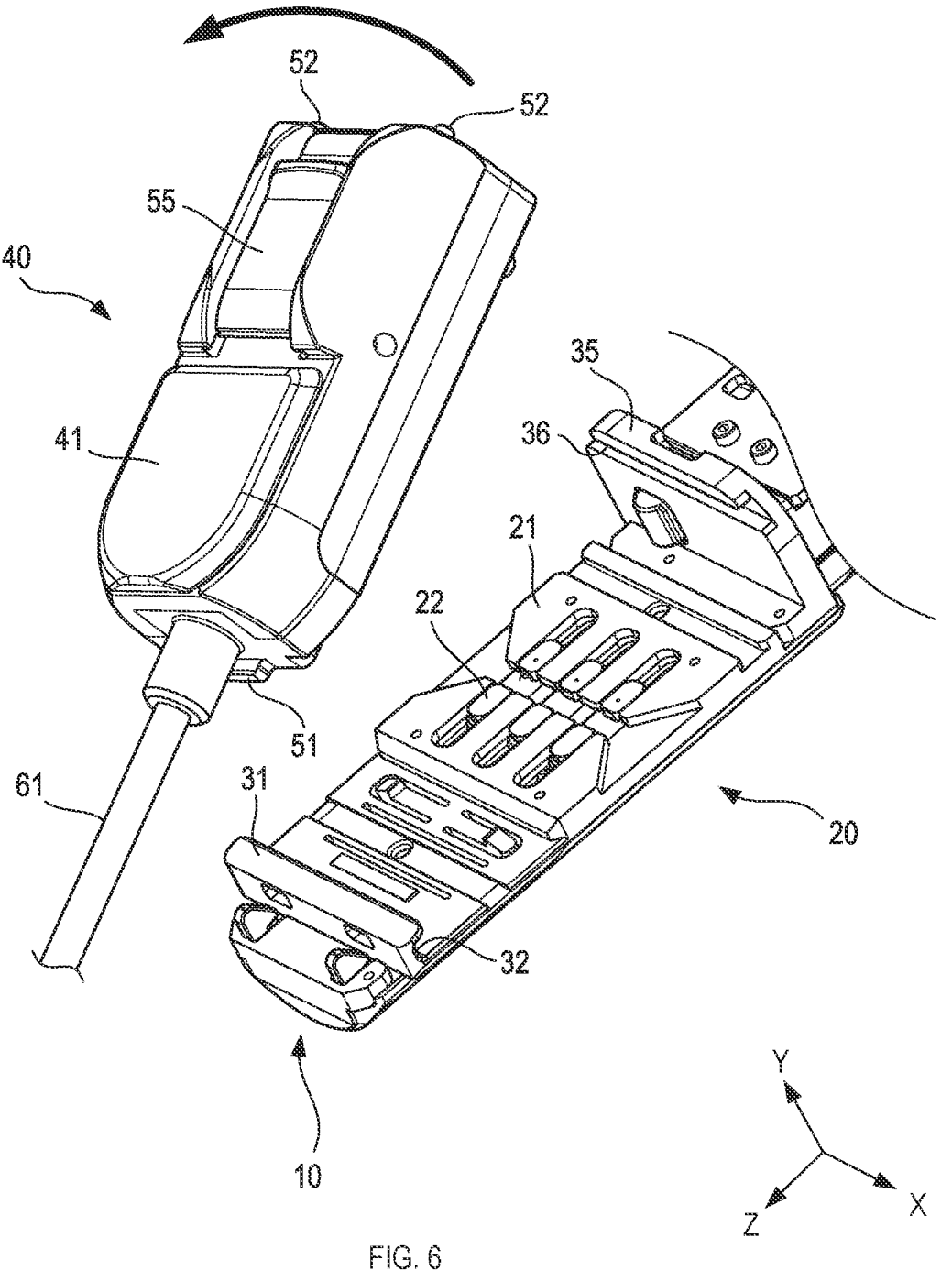
FIG. 6 is a partial perspective view illustrating detachment of the surgical tool in the medical robot in FIG. 1.

Then, as shown in FIG. 6, an end of the surgical tool 40 on the negative direction side of the Z-axis is raised in a direction of departing from the adapter 20, specifically in the positive direction of the Y-axis. Subsequently, the surgical tool 40 as a whole is raised in the positive direction of the Y-axis, and the first surgical tool engagement portion 51 is pulled out from the first engagement groove 32. As a result, detachment of the surgical tool 40 from the adapter 20 is completed.

According to the medical robot 1 and the adapter 20 configured as described above, the surgical tool 40 may be attached to the adapter 20 by relative movement between the surgical tool 40 and the adapter 20 in a direction along the attachment surface 21 and intersecting a linear motion direction of the driven portions 43 and the transmission plates 22. Also, the driven portions 43 are guided to the specified positions in the transmission side holes 24 when attaching the surgical tool 40 to the adapter 20.

In comparison with, for example, the configuration disclosed in Patent Document 1, the transmission plate 22 and the driven portion 43 may be engaged with each other by a simple configuration since it is unnecessary to use a biasing mechanism. Also, there is less need to provide a gap between the transmission plate 22 and the driven portion 43, thus facilitating secure engagement therebetween.

Further, since the gap may be reduced, increase in operability of the medical robot 1 is facilitated. Moreover, reduction of the gap facilitates transmission of an external force, which is a force applied to the forceps 65 of the surgical tool 40, to the medical robot 1, and facilitates increase in accuracy when estimating the external force. For example, it is possible to facilitate increase in safety of surgeries using the medical robot 1, and to facilitate reducing occurrence of complications. In other words, it is possible to facilitate improved QOL of patients, and to facilitate reducing burden on doctors who operate the medical robot 1. "QOL", referred to herein, is an abbreviation of "Quality of Life". Moreover, it is possible to facilitate achievement of an improved learning curve in surgeries using the medical robot 1.

In addition, it is possible to determine whether arrangement relationships of the transmission plates 22 and the driven portions 43 are each a desired arrangement relationship based on a relative position of the surgical tool 40 and the adapter 20. Examples of the desired arrangement relationship may include an arrangement relationship that allows transmission of a driving force. In other words, there is less need to use a detection device, such as a sensor and a switch, than in the configuration disclosed in Patent Document 1. Accordingly, it is possible to reduce complication of the configuration caused by providing the detection device, and to facilitate downsizing of the medical robot 1.

By providing the introducing groove 26 to the guide groove 25, the projection 44 of the driven portion 43 is guided by the introducing groove 26 and thus is facilitated to enter the guide groove 25 when attaching the surgical tool 40 to the adapter 20. Also, in a case where the introducing groove 26 is provided at each of both ends of the guide groove 25, as compared with a case of being provided at one end, there is an increased degree of freedom in terms of an approaching direction of the surgical tool 40 to the adapter 20, and thus attachment of the surgical tool 40 is facilitated.

By providing the actuators 11, the transmission plates 22 may be easily arranged at the specified positions when attaching the surgical tool 40 to the adapter 20. As compared with a case without the actuators 11, workload may be reduced when attaching the surgical tool 40 to the adapter 20, and thus attachment is facilitated.

By providing the transmission side holes 24 and the transmission plates 22 side by side along a relative movement direction of the surgical tool 40 and the adapter 20, and providing the driven side holes 42 and the driven portions 43 so as to correspond to at least a part of the transmission side holes 24 and the transmission plates 22, it is possible to transmit different driving forces to the forceps 65 using a plurality of combinations of the transmission plates 22 and the driven portions 43. Accordingly, it is possible to control a plurality of actions of the forceps 65.

By providing the recessed portion 23 to the transmission plate 22, it is possible to engage the projection 44 of the driven portion 43 with the recessed portion 23 of the transmission plate 22 when the surgical tool 40 is attached to the adapter 20. Also, it is possible to transmit a driving force from the transmission plate 22 to the driven portion 43 based on the engagement of the projection 44 with the recessed portion 23.

It is to be noted that the technical scope of the present disclosure is not limited to the aforementioned embodiment, and various modifications may be made without departing from the subject matter of the present disclosure. For example, although the aforementioned embodiment is described employing a configuration where the surgical tool 40 may be attached from the positive direction side of the X-axis or may be attached from the negative direction side of the X-axis, it may be possible to employ a configuration where the surgical tool 40 is attachable only from the positive direction side of the X-axis, or only from the negative direction side of the X-axis.

Also, although the transmission plate 22 is moved to the specified position using the actuator 11 in the present embodiment, a biasing member, such as a spring, may be used in place of the actuator 11 when moving the transmission plate 22 to the specified position.

Further, although the driver 10 and the adapter 20 are attachable to and detachable from each other in the present embodiment, a component equivalent to the adapter 20 may be integrated with the driver 10, and there is no particular limitation therefor.

While various embodiments have been illustrated and described above, it will be apparent to those skilled in the art that modifications and variations may be made without departing from the scope defined by the appended claims.

What is claimed is:

1. A medical robot comprising:
   a surgical tool comprising:
      a main body comprising:
      a driven plate configured to transmit a driving force to a treatment portion for performing a medical treatment; and
      a driven side hole in which the driven plate is housed and in which the driven plate is arranged so as to be linearly movable; and
      an attachment portion comprising:
      an attachment surface configured to face a surface of the main body in which the driven side hole is provided; and
      a transmission side hole in which a transmission plate is arranged that transmits the driving force in a linear motion direction to the driven plate,
   wherein the surgical tool and the attachment portion respectively comprise a surgical tool engagement portion and an attachment engagement portion configured to attach the surgical tool to the attachment portion by relative movement of the surgical tool and the attachment portion in a relative movement direction that is parallel to the attachment surface and that intersects the linear motion direction, and wherein the attachment surface comprises a guide groove extending laterally in the relative movement direction and configured to engage with a projection projecting from the driven plate when attaching the surgical tool to the attachment portion, thereby guiding the driven plate to a specific position of the transmission side hole.

2. The medical robot according to claim 1, further comprising an introducing groove provided at least at one end of the guide groove along the relative movement direction, the introducing groove having a greater groove width in a direction away from the transmission side hole.

3. The medical robot according to claim 1, further comprising an actuator configured to move the transmission plate to the specific position.

4. The medical robot according to claim 1, wherein a plurality of the transmission side holes and a plurality of the transmission plates are provided in the attachment portion side by side along the relative movement direction, and wherein a plurality of the driven side holes and a plurality of the driven plates are provided in the main body so as to correspond to at least a part of the plurality of the transmission side holes and the plurality of the transmission plates.

5. The medical robot according to claim 1, wherein the transmission plate comprises a recessed portion configured to engage with the projection of the driven plate in response to attachment of the surgical tool to the attachment portion, the recessed portion including an opening that allows the projection to move along the relative movement direction.

6. The medical robot according to claim 1, wherein the specific position is an engagement position at which the driven plate engages with the transmission plate.

7. The medical robot according to claim 1, wherein the treatment portion comprises a forceps or an endoscope.

8. The medical robot according to claim 1, wherein the surgical tool engagement portion is a first surgical tool engagement portion and the attachment engagement portion is a first attachment engagement portion, the surgical tool further comprises a second surgical tool engagement portion and the attachment portion further comprises a second attachment engagement portion, and wherein, when the surgical tool is attached to the attachment portion, the second surgical tool engagement portion engages with the second attachment engagement portion to restrict movement of the surgical tool in a direction orthogonal to the linear motion direction and an attachment direction.

9. A medical robot comprising:

a surgical tool comprising:

a main body comprising:

a driven plate that transmits a driving force to a treatment portion;

a first hole in which the driven plate is housed and in which the driven plate is movable in a linear direction;

a projection provided on the driven plate; and an engagement projection provided at a distal end of the main body, the engagement projection extending in an intersecting direction that is parallel to a surface of the main body in which the first hole is formed and that intersects with the linear direction; and an adapter comprising:

a transmission plate configured to transmit the driving force to the driven plate;

a second hole in which the transmission plate is housed and in which the transmission plate is movable in the linear direction;

a guide groove that extends in the intersecting direction; and an engagement groove provided at a distal end of the adapter, the engagement groove extending in the intersecting direction and parallel to a surface of the adapter in which the second hole is formed, wherein the surgical tool is configured to be attached to the adapter by relative movement laterally in the intersecting direction, and wherein, when the surgical tool is attached to the adapter, the guide groove engages with the projection and the engagement groove engages with the engagement projection to guide the driven plate to a position within the second hole.

10. The medical robot according to claim 9, wherein the adapter further comprises an introducing groove in communication with the guide groove and provided at one end of the guide groove in the intersecting direction, the introducing groove having a width that increases as a direction from the second hole increases.

11. The medical robot according to claim 9, further comprising an actuator configured to move the transmission plate to the position within the second hole.

12. The medical robot according to claim 9, wherein the transmission plate comprises a recess configured to engage with the projection, the recess allowing the projection to move along the intersecting direction when the surgical tool is attached to the adapter.

13. The medical robot according to claim 9, wherein the position within the second hole is an engagement position at which the driven plate engages with the transmission plate.

14. The medical robot according to claim 9, wherein the adapter comprises a plurality of the second holes and a plurality of the transmission plates spaced apart from each other in the intersecting direction, wherein the surgical tool comprises a plurality of the first holes and a plurality of the driven plates spaced apart from each other in the intersecting direction, and wherein, when the surgical tool is attached to the adapter, the guide grooves engage with the projections to guide the driven plates to positions within the second holes.

15. The medical robot according to claim 9, wherein the treatment portion comprises a forceps or an endoscope.

16. The medical robot according to claim 9, wherein the surgical tool further comprises a plurality of engagement protrusions at a proximal end of the surgical tool, and wherein the adapter further comprises a proximal engagement groove at a proximal end of the adapter, and wherein, when the surgical tool is attached to the adapter, the plurality of engagement protrusions engage with the proximal engagement groove to restrict movement of the surgical tool in a direction orthogonal to the linear direction and the intersecting direction.

17. A medical robot comprising:

a surgical tool comprising:

a main body comprising:

a driven portion configured to transmit a driving force to a treatment portion for performing a medical treatment; and a driven side hole in which the driven portion is housed and in which the driven portion is arranged so as to be linearly movable; and an attachment portion comprising:

an attachment surface configured to face a surface of the main body in which the driven side hole is provided; and a transmission side hole in which a transmission plate is arranged that transmits the driving force in a linear motion direction to the driven portion, wherein the surgical tool and the attachment portion respectively comprise a surgical tool engagement portion and an attachment engagement portion configured to attach the surgical tool to the attachment portion by relative movement of the surgical tool and the attachment portion in a relative movement direction that is parallel to the attachment surface and that intersects the linear motion direction, and wherein the attachment surface comprises a guide groove extending laterally in the relative movement direction and configured to engage with a projection projecting from the driven portion when attaching the surgical tool to the attachment portion, thereby guiding the driven portion to a specific position of the transmission side hole.

* * * * *